United States Patent [19]
Wulf et al.

[11] 4,015,943
[45] Apr. 5, 1977

[54] APPARATUS FOR THE ESTERIFICATION OF TEREPHTHALIC ACID IN THE GAS PHASE

[75] Inventors: Horst-Dieter Wulf; Ferdinand List, both of Marl; Friedrich-August Orlowski, Haltern; Norbert Wilke; Emmerich Pflegerl, both of Marl, all of Germany

[73] Assignee: Chemische Werke Huls Aktiengesellschaft, Marl, Germany

[22] Filed: Apr. 21, 1976

[21] Appl. No.: 679,046

Related U.S. Application Data

[62] Division of Ser. No. 420,307, Nov. 29, 1973, Pat. No. 3,972,912.

[30] Foreign Application Priority Data

Dec. 15, 1972 Germany .......................... 2261333

[52] U.S. Cl. .................................... 23/262; 23/279
[51] Int. Cl.² ...................... B01J 8/04; C07C 69/76
[58] Field of Search ................. 23/260, 262, 288 R, 23/288 E, 286, 279; 260/475 R

[56] References Cited

UNITED STATES PATENTS

| 3,072,465 | 1/1963 | Benichou et al. | 23/288 R |
| 3,227,743 | 1/1966 | Shaw et al. | 260/475 R |
| 3,364,251 | 1/1968 | Benning et al. | 260/475 R |
| 3,377,376 | 4/1968 | Gainer et al. | 260/475 R |
| 3,617,226 | 11/1971 | List et al. | 260/475 R |
| 3,676,485 | 7/1972 | Lewis et al. | 260/475 R |
| 3,844,934 | 10/1974 | Bomacci et al. | 23/288 R X |

FOREIGN PATENTS OR APPLICATIONS

| 1,933,946 | 1/1971 | Germany | 260/475 R |
| 1,212,063 | 3/1966 | Germany | 260/475 R |
| 1,110,684 | 4/1968 | United Kingdom | 260/475 R |

Primary Examiner—Joseph Scovronek
Assistant Examiner—Arnold Turk
Attorney, Agent, or Firm—Gilbert L. Wells

[57] ABSTRACT

Dimethyl terephthalate is prepared by the continuous esterification of terephthalic acid in the gas phase by evaporating solid terephthalic acid in a pre-reactor by means of a hot methanol vapor stream, conducting the gas mixture through a solid bed catalyst in a follow-up reactor, and recirculating a portion of the reaction product to the pre-reactor. After the pre-reactor the terephthalic acid dispersed in the methanol gas phase is heated and vaporized in one or more consecutive heat exchangers followed by one or more dwell period lengths and immediately heated to the esterification temperature prior to entry into the follow-up reactor.

1 Claim, 1 Drawing Figure

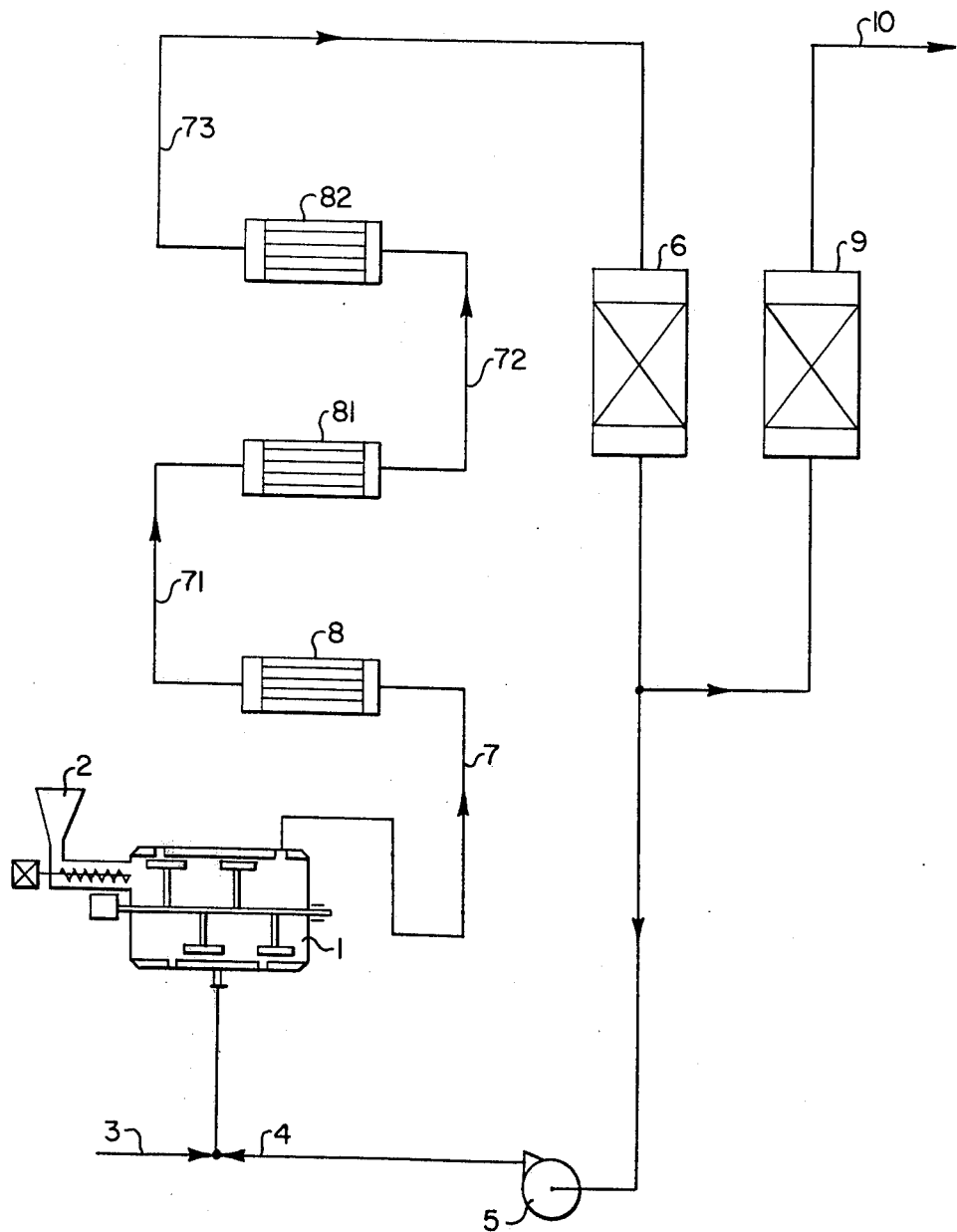

APPARATUS FOR THE ESTERIFICATION OF TEREPHTHALIC ACID IN THE GAS PHASE

CROSS REFERENCES TO RELATED APPLICATIONS

This is a division of application Ser. No. 420,307, filed Nov. 29, 1973, now U.S. Pat. No. 3,972,912.

Applicants claim priority under 35 U.S.C. 119 for Application Ser. No. P 22 61 333.8, filed Dec. 15, 1972, in the Patent Office of the Federal Republic of Germany.

The disclosure of U.S. application Ser. No. 361,597, filed May 18, 1973, now U.S. Pat. No. 3,940,431, is incorporated herein. Application Ser. No. 361,597 discloses the state of the art of preparing dimethyl terephthalate by the esterification of terephthalic acid in the gaseous phase.

The disclosure of U.S. application Ser. No. 389,793, filed Aug. 30, 1973, now U.S. Pat. No. 3,907,709, entitled "Esterification Catalysts" and having as inventors Ferdinand List and Kurt Wember is incorporated herein. This application discloses the state of the art of silica gel esterification catalysts useful in the present invention.

Application Ser. No. 39,761, filed May 22, 1970, now abandoned and corresponding to West German published Application 1,933,946 is also incorporated herein.

BACKGROUND OF THE INVENTION

The field of the invention is esters and processes of making the same from polycarboxylic acids. The present application is particularly concerned with the preparation of dimethyl terephthalate by the esterification of terephthalic acid.

The state of the art of preparing dimethyl terephthalate may be ascertained by reference to the Kirk-Othmer "Encyclopedia of Chemical Technology". 2nd Ed., Vol. 15(1968), pages 466–467, under the section "Current Commercial Processes for Polymer-Grade Dimethyl Terephthalate," and by reference to U.S. Pat. Nos. 2,876,252 of Rudolf Lotz et al, which issued Mar. 3, 1959; 3,617,226 of Ferdinand List et al, which issued Nov. 2, 1971; and 3,364,251 of Anton Benning et al which issued Jan. 16, 1968; British Pat. No. 1,053,164 published Dec. 30, 1966; German Published Application 1,667,430 corresponding to French Pat. 1,585,305; and German Published Application 1,933,946 of Ferdinand List and Helmut Alfs, published Jan. 21, 1971, the disclosures of which are incorporated herein.

The state of the art of fluidized beds, particularly for use in catalysts and gas-solid reactions, may be ascertained by reference to Kirk-Othmer ibid, Vol. 9 (1969), under the section "Fluidization," pages 398–445.

The present invention is particularly concerned with a process for the continuous esterification of terephthalic acid with methanol in the gas phase in a system consisting of a pre-reactor and a connecting solid bed catalyzer.

The use of terephthalic acid as the basic material for the production of polyester fibers is well known. Since the acid, in the usual commercial production process is not produced as purely as is required for the polycondensation reaction, purification methods must be added to the production which can effectively remove the unfavorable physical properties of commercial terephthalic acid. In most cases, the purification of the acid is undertaken in the form of its dimethyl ester which can be introduced with the regeneration of methanol to the interchange of ester radicals and the preliminary condensation with glycol or other dioles.

Therefore, there is a considerable interest in an efficient process for esterifying terephthalic acid. Methanol, because of its light molecular weight and its low cost, is the most favorable alcohol component, although the esterification with methanol poses special technical problems of a chemical nature. Terephthalic acid, itself is practically insoluble in boiling methanol, and the esterifiction can be executed with sufficient speed only in pressure resistant apparatus made of high alloy steel.

Therefore, a process has been developed whereby terephthalic acid is esterified in the gas phase with superheated methanol vapor, in part by adding inert gas as a carrier gas. This process is disclosed in U.S. Pat. No. 2,876,252, whereby pulverulent terephthalic acid is reacted with methanol at approximately 300° C, by spraying catalytic mixtures of the acid and methanol into a reaction tube, to yield relatively little output of a dimethyl terephthalate of little purity. According to U.S. Pat. No. 3,364,251, methanol, and if necessary with nitrogen added, is fed upwards into a fluidized bed of catalysts and pulverulent terephthalic acid, and the dimethyl ester, quickly formed at the high reaction temperatures of approximately 300° C, is discharged in the form of gas, together with the excess methanol and the water of reaction. The dynamic conditions of the fluidized bed are, however, disadvantageous for general use: the particle size distribution of the injected terephthalic acid and the whirling conduct of the acid and the esterification catalyst can bring about an undesired channel formation and must be adjusted to each other within a relatively narrow margin, to prevent one of the two components or parts thereof from being discharged earlier from the reactor.

British Pat. No. 1,053,164 demonstrates the esterification of terephthalic acid after vaporization in the superheated methanol vapor stream in contact with a solid catalyst. Thereby, pelleted terephthalic acid becomes vaporized from a 315° to 345° C heated sublimation zone with methanol of approximately 400° C, and is esterified in a follow-up reactor at approximately 300° C. For the process of heating and vaporizing the terephthalic acid that is brought into the sublimator, the thermal conductivity of the superheated methanol can be used. This, in itself simple, process of esterification requires a tenfold amount by weight of methanol at 400° C and also a continuously operating sublimator, in order to heat the terphthalic acid of aproximately 20° C to an average sublimation temperature of 330° C and to completely vaporize it at this temperature.

On the other hand, in the process according to U.S. Pat. 3,617,226, whereby pulverulent terephthalic acid is mechanically mixed with a suitable solid catalyst in a horizontal cylindrical container and exposed to methanol in the gaseous phase from 300° to 320° C, the particle size of the esterification catalyst and acid need not be correlated, and the resulting terephthalic acid dimethyl ester leaves the reactor in the gaseous state. Since, at these reaction temperatures, the esterification speed is extremely high, the transformation of the terephthalic acid and volume-time output become dependent upon technical process factors such as velocity of diffusion, the ratio of the catalytically active surface to the terephthalic acid, transportation of material and heat, dwell, et al. Dwell and transformation are, in the first approach, dependent upon the catalyst surface available for the time unit and the amount of heat which is needed to vaporize the terephthalic acid and the dimethyl terephthalate, respectively. In this case, the catalyst surface, available per unit of time, is determined by the useful volume of the cylindrical vessel, while the transferable amount of heat, apart from the possible temperature difference between the heating medium and the reactants, is limited by its surface. By enlarging these cylindrical reactors, however, the ratio of the surface to the volume becomes smaller, so that for great esterification capacities a limitation occurs because of the technical possibilities of producing cylindrical reactors with the highest possible heat surfaces and stirring devices.

SUMMARY OF THE INVENTION

Overcoming this technical limitation is an object of the present invention. But, generally, it is also part of the present invention to make better operable such processes whereby terephthalic acid is totally or partly vaporized in a methanol vapor stream and consequently esterified in contact with a solid bed of catalysts.

A further object of the present invention is to achieve the greatest possible terephthalic acid transformation with a minimum methanol excess. It stands to reason that one strives for the complete transformation of the terephthalic acid for the purpose of exhausting a given function such as for the simplification of the total use of the reaction mixture.

The esterification of terephthalic acid occurs in two steps:

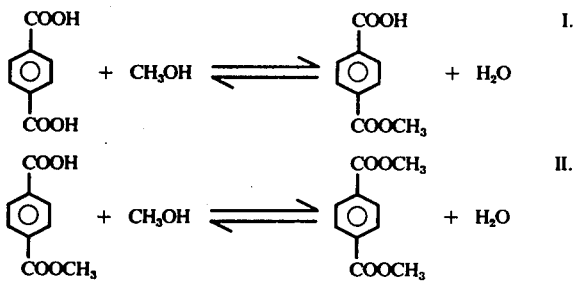

The terephthalic acid monomethyl ester, formed according to equation I, $Kp_{760} 303°$, is completely vaporized at the given reaction temperatures and it is unavoidably discharged with the product stream when the apparatus is further loaded. It was, therefore, significant not to use up a gas stream immediately which contains this monoester, but to transform it, with the remaining excess of methanol in a secondary reactor which contains the same catalyst as the main reactor, as solid flow. A procedure of this sort is disclosed in West German Published Application 1,933,946, corresponding to U.S. application Ser. No. 39,761, filed May 22, 1970, whereby the total esterification results in the bed of solids, while the rotary oven serves for distribution and partial vaporization of the solid terephthalic acid in the methanol vapor. When an apparatus consisting of a rotary oven, such as disclosed in U.S. Pat. No. 3,617,226, coupled with a follow-up reactor, as shown in FIG. 1 of application Ser. No. 361,597, is being fed with methanol and increasing amounts of terephthalic acid, then it is likewise unavoidable that portions of the finely pulverulent terephthalic acid with particle sizes as small as 5 $\mu$ are carried along. This contributes to the catalyst flow in the follow-up reactor and this results in an increase of differential pressure between entry and exit, and can in extreme cases, lead to clogging. Besides the solid particles carried through, the entrance of the follow-up reactor can also be stopped up when the reaction mixture is saturated with terephthalic acid vapor in the main reactor at the therein existing temperatures, and part of this vaporized terephthalic acid, because of very low cooling, condenses on the walls of the follow-up reactor, especially at the entrance.

These restrictions can be suppressed or removed by using a satisfactory and highly heated amount of methanol vapor for the complete vaporization of the terephthalic acid. It is, however, obvious that by increasing the methanol amount, the economy of the process can be impaired, since for the vaporization and superheating to recover the methanol, a considerable amount of heat is used. On the other hand, the superheating of the methanol is restricted to approximately 330° C. At higher temperatures, we see a sharp increase in the up-to-here very minor disintegration on the catalytic surfaces into dimethyl ether, formaldehyde and methane. And not least of all, all these temperatures the technical problems grow which originate with the heating with highly superheated steam or heat carriers.

It is, therefore, a further object of the present invention to simply but surely avoid these possible difficulties.

The invention solves this problem by recirculating a partial stream of the hot, gaseous esterification mixture from the outlet of the system into the pre-reactor by dispersing the terephthalic acid in this gas stream, together with fresh methanol vapor in the reactor, by heating and vaporizing it in one or more consecutive heat exchangers that at times are followed by a dwell length, and by immediately heating it to the esterification temperature and by then feeding it in vaporized form through the solid bed of catalysts.

BRIEF DESCRIPTION OF THE DRAWING

The invention may best be described by reference to the drawing, wherein:

The FIGURE is a diagrammatic representation of an embodiment of the apparatus of the present invention showing an improvement of the apparatus of application Ser. No. 39,761.

DESCRIPTION OF THE PREFERRED EMBODIMENTS

The hot, gaseous esterification mixture consists of dimethyl terephthalate, methanol and reaction water besides traces of monomethyl terephthalate; the partial stream, detoured and led back into the preliminary reactor, takes up, together with the fresh methanol vapor, non-esterified terephthalic acid until it reaches the complete partial vapor pressure. The recirculated quantity whose terephthalic acid vaor pressure equals zero, is purposely chosen so that all non-esterified terephthalic acid can enter into the vapor phase.

Since this gas stream, after complete esterification of the terephthalic acid, contains a 1 : 2 molar ratio of ester product:water which are likewise returned into the esterification zone, it could be expected that the esterification balance would at least shift slightly to the side of the free acid, especially since precautions are taken in the invention to keep the methanol excess at the lowest possible level. Also a decrease of esterification velocity is to be expected. Surprisingly, the practical result is a terephthalic acid transformation degree of more than 99 percent which can, if necessary, be increased further by inserting more follow-up reactors into the main product stream.

A particularly useful terephthalic acid is a fine crystalline powder, whose particle size distribution lies between about 5 and 300 mm, wherein the largest particle diameter is found to be between about 70 and 110 mm, which accumulates after drying according to the known process according to the state of the art. In this particular example one can use a rotating oven as disclosed in Application Ser. No. 39,761. in this particular case before the entry of the gaseous mixture into the fixed bed catalyst there is very little esterification, i.e. the gaseous mixture contains besides fresh and recirculated methanol, recirculated dimethylterephthalate and recirculated reaction water, yet the vaporized terephthalic acid is substantially unesterified.

Vaporization here means the total transfer of the solid terephthalic acid into the vapor phase, so that the progress of the process consists of avoiding the conduction of the solid, finely dispersed terephthalic acid by the carrier-gas stream.

For vaporization, e.g. pre-reactor or a rotary furnace according to Application Ser. No. 39,761 are used having agitators, whirling chambers, and other technical devices which allow a distribution of the pulverulent solids into a gas stream. In this prereactor, solid pulverulent terephthalic acid is dispersed in methanol and rotating gas of approximately 330°, and the mixture is fluidized so that it behaves like a gas and can, without separating into solid and gaseous particles, be transported at the above-mentioned velocities through normal tubings and conventional tube heat exchangers. Such a dispersion (fluidized bed) is obtained by intimately mixing the fine terephthalic acid powder with the gaseous reaction discharge and fresh methanol. The heat exchangers and tubings through which this dispersion flows are so dimensioned that flow velocities of approximately 3 to 5 meters per second, especially 7 to 8 meters per second, are reached.

Surprisingly, it is not difficult to set up such gas velocities by adjusting the sizes of the apparatus and the throughput velocities, so that solid terephthalic acid discharged from a fluidized bed apparatus is completely vaporized in subsequent heat exchangers and dwell extensions, without settling or caking.

Purposely, in order to avoid an unnecessary use of energy, the reaction discharge is taken from the exit of the esterification reactor where it accrues in gas form at temperatures from 300° to 320°, and it is led back into the preliminary reactor as a branch stream by using a rotating gas blast apparatus or diffuser. Thereby, this reaction discharge can furthermore be heated through heat exchangers. It is peculiar to the present process that, under the conditions of the invention, also the solids-containing gas stream can be heated in heat exchangers of customary and known design without any disadvantages.

All pipe lines and heat exchangers are so dimensioned that the heat transferred during the given dwell time in the pipes can be fully used for the vaporization of the terephthalic acid. Since the sublimation of the terephthalic acid, i.e. the transition of the acid from the solid into the gaseous state, does not happen instantaneously but requires a definite measurable time, it is unsuitable and expendable to supply the total heat necessary, i.e. 0.27 Kcal/kg for the vaporization, through a single heat exchanger, because the absorbed heat, while passing through the tube, can only partly lead to vaporization of the solid particles. It appears that either the heat exchanger must be considerably overdimensioned or that, with a normal design, solid terephthalic acid discharges after the heat exchanger. This discharged terephthalic acid can settle in the apparatus following if the possibility of transforming the absorbed heat into vapor is not permitted as a result of isolation and formation of free paths. Measurements show that terephthalic acid having an average of 100 microns particle diameter needs 1 to 3 seconds for vaporization. It is also suitable to transfer the necessary heat in 2 or more heat exchangers and to take care that in the subsequent dwell periods the heat of vaporization can be utilized. The cross sections and lengths of the tubings which constitute these dwell periods must be chosen so that, for a given throughput performance, the above-mentioned flow velocities of 3 to 15 meters per second are achieved and that the dwell period in the heat exchanger and in the subsequent dwell time stretch, and in a system consisting of several heat exchangers and dwell time stretches respectively, last 1 to 8, preferably 2 to 3 seconds.

Preferably, it is constructed so that the total terephthalic acid in the subsequent heat exchangers is vaporized below 350° C, particularly below 330° C.

As solid catalysts, the following are suitable: silicates, oxides, hydroxides and phosphates, as mentioned for example in U.S. Pat. No. 3,617,226, and especially silica gel pearls with low aluminum oxide and alkali content, as described in West German Published Application 1,667,430.

The advantages of the invention are as follows:

One can see from the following Table I that the vapor pressure of the terephthalic acid, at 320°, amounts to 20.0 Torr (mm.Hg).

TABLE I

| Vapor pressure of terephthalic acid | |
|---|---|
| 290° C | 4.5 Torr |
| 300° C | 7.5 Torr |
| 310° C | 13.0 Torr |
| 315° C | 16.7 Torr |
| 320° C | 20.0 Torr |
| 325° C | 27.0 Torr |
| 330° C | 32.0 Torr |

At the collective pressure of 1,100 Torr (= approximately 0.5 atmosphere excess pressure), produced in the pre-reactor by the flow resistances of the following apparatus, there are e.g. at 320° C interior temperature at the maximum 1.95 molar percent of terephthalic acid vapor in the gas stream. i.e. the methanol vapor must amount to at least 98.15 metric ton of terephthalic acid per hour.

In order to keep an aqueous methanol mixture of terephthalic acid dimethyl ester so that it can be transported as it is produced by cooling the reaction gases according to the esterification apparatus, the solid part may be 25 to 30 percent by weight, i.e. from this a terephthalic acid : methanol ratio should not be more than 1 : 3 parts by weight. In practice, the maximum vaporizable amount of the transformation of terephthalic acid into dimethyl terephthalate and monomethyl terephthalate, depends on the degree of saturation of the vapor with terephthalic acid and upon the velocities of the heat transfer in the unit of time. Since all inlet sizes mentioned are functions of additional variables, an exact calculation of the maximum vaporizable terephthalic acid is not practically possible. In the following Table II, values are compiled for a methanol: terephthalic acid ratio of 3.0 and a degree of saturation of 100 percent.

TABLE II

Maximum amount of vaporizable terephthalic acid at a terephthalic acid : methanol ratio by weight of 1:3.

(R = Ratio of the recirculated to the injected molecular mass;

kg/t = vaporizable amount in kilograms per metric ton of injected terephthalic acid

| Temp,° C | R - Mole % | Maximum vaporizable amount of terephthalic acid at | | | |
|---|---|---|---|---|---|
| | | 0 kg/t | 1 kg/t | 2 kg/t | 3 kg/t |
| 300 | 0.69 | 1.07 | 220 | 334 | 448 |
| 310 | 1.19 | 184 | 384 | 582 | 780 |
| 315 | 1.51 | 240 | 495 | 750 | 1036 |
| 320 | 1.85 | 288 | 595 | 901 | 1207 |
| 325 | 2.32 | 362 | 747 | 1132 | 1517 |
| 330 | 3.00 | 472 | 967 | 1461 | 1957 |

From Table II it follows that at temperatures of 330° C and at a return ratio of 1.1, all non-transformed terephthalic acid can be vaporized and returned to the post-reactor with the gas stream.

The process described above succeeds for example by means of the arrangement depicted in the drawing wherein:

At temperatures of around 330° C and via the tubing 2, terephthalic acid is measured out into an externally heated cylindrical container 1. Via the tubing 3, and especially in tangential direction, the following are fed into the reactor: the 2- to 5-fold, particularly the 3-fold amount by weight relative to terephthalic acid, of methanol vapor of 300° to 330° C; and via the tubing 4 and a blower 5, from the exhaust of the esterification pre-reactor 6, relative to methanol similarly up to a 5-fold amount by weight of a crude gaseous esterification mash, mainly consisting of terephthalic acid dimethyl ester, methanol and reaction water with a temperature of around 330° C. The pulverulent terephthalic acid is thereby heated and partially vaporized and leaves the mash container via tubing 7, together with the gas mixture in the form of very fine solid particles which are light enough to be suspended in the gas stream at the existing flow velocity, while the larger solid particles, only after partial vaporization, are made smaller to the extent that they can also be carried out with the gas stream.

Via a dwell period extension and a heat exchanger or via a system of dwell period extensions 7,71,72,73 and heat exchangers 8,81,82, sufficient heat is fed into the gas stream containing solid terephthalic acid so that the total terephthalic acid evaporates, to produce a solid-free gas stream supply to the esterification pre-reactor 6. The esterification occurs at temperatures of between 280° and 350° C, preferably at 320° to 330° C with solid catalysts, as described in U.S. Pat. No. 3,617,226, with a terephthalic acid conversion of up to 96 to 99 percent. Behind the esterification pre-reactor 6, the gas stream is divided: one part arrives back in the mixing vessel via the conduit 4 and the blower 5, while another part is completely esterified in the follow-up reactor 9 and the product is collected via the conduit 10.

The object of the present invention to supply solid terephthalic acid at room temperature with sufficient heat that it evaporates without disintegration and without formation of solid sediment and clogging for entry into the pre-reactor is achieved with the following variables:

terephthalic acid particle size of about 5 to 300$\mu$m, preferably 70 to 200 and especially 110 to 150$\mu$m;

dwell time in the heat exchangers and dwell period extensions of about 1 to 8 seconds, preferably 2 to 6 seconds and especially 2 to 3 seconds; and temperature range of vaporized terephthalic acid: methanol mixture leaving end of heat exchanger/dwell period extensions and entering pre-reactor of about 250° to 350° C, preferably 300° to 350° C, and especially 310 to 330° C.

EXAMPLE

In an apparatus constructed according to the drawing, the mixing vessel 1 which is heated through the casing jacket, is, via the conduit 2, hourly supplied with 50 kg of terephthalic acid with particle sizes of approximately 20 to 150 micrometers in diameter at a temperature of 25° C. Every hour, via the pipe line 3, 150 kg of methanol vapor at 330° C and, via the pipe line 4, 450 kg of circulation gas at 330° C reach the mixing vessel. After thorough mixing and partial evaporation of the solid terephthalic acid in the gas stream, the temperature reaches 305° to 310° C at the exit of the vessel. After passing the first heat exchanger 8 and the first dwell period extension 71, the mixture reaches the temperature of 318° to 322° C; after the second heat exchanger 323° to 325° C, and after the third heat exchanger, at the entrance into the esterification reactor, 328° to 333° C. Thereby, the dwell period extensions 7, 71, 72 and 73 are so dimensioned that average dwell periods of 1.0, 0.5 and 0.2 seconds are reached, not including the dwell periods in the heat exchangers themselves. The vaporized terephthalic acid is esterified at temperatures of around 330° C in contact with solid silica gel catalysts, with 96 to 99 percent output. The reaction product is separated into divided streams of which the one runs into the mixing vessel via the blower 5, while the other is esterified with approximately 200 kilograms per hour post-reactor 9 with the residual terephthalic acid content of 0.1 to 0.3 percent, and then, used to form pure dimethyl terephthalate.

This example shows the mode of the process of the present invention and its use is not limited to the chosen ratios of amount, temperature and dwell period. Much more decisive is the compliance with definite ratios of the recycling quantity at a given temperature for the complete vaporization of the terephthalic acid as set forth in detail in Application Ser. No. 361,597 and the dwell periods adjusted to the vaporization time of the distinctly large terephthalic acid particles before the gas stream enters the esterification reactor.

When for the esterification a terephthalic acid with a small average grain diameter, e.g. from 20 to 30 micrometers is used, then the necessary total dwell time in the vaporization periods lessens to approximately 1.0 seconds; the time increases to 5 to 6 seconds when terephthalic acid with grain sizes of 300 and more micrometers is injected. Suitably, for this esterification process, terephthalic acid with the smallest particle diameter of not less than approximately 5 and not more than approximately 300 micrometers is used. Especially proper is a terephthalic acid whose particle size is mainly between 30 and 150 micrometers, as it is produced in most commercial processes.

The process of the present invention is exceedingly advanced and surprising. On the one hand, since for every molecule of esterified terephthalic acid 2 moles of water result, it is to be expected that the esterification equilibrium would be at least slightly shifted to the side of the free acid, and especially, according to the invention, that the methanol excess must be kept small. Surprisingly, practice has taught that also by using this aqueous reaction discharge as circulation gas, esterification rates of more than 99 percent are obtained. On the other hand, there is the problem to be solved of supplying solid terephthalic acid at room temperature with so much heat that it evaporates both without disintegration and without formation of solid sediment and clogging. This problem is easily solved if the above-mentioned conditions are adhered to.

We claim:

1. An apparatus for the esterification of a normally solid organic acid in the solid state with normally liquid alcohol in the gaseous or vapor state, to an ester in the presence of a granular solid esterification catalyst, which consists essentially of a rotatable tunnel oven;
   means for heating said tunnel oven;
   means for feeding said organic acid in the solid state into one end of said oven;
   means for feeding said alcohol into said one end of said oven;
   means for discharging a gaseous current of alcohol and said acid from the other end of said oven;
   an esterification pre-reactor having a fixed bed catalyst;
   means for forwarding the gaseous current of alcohol and said acid from said means for discharging to said pre-reactor, said fowarding means comprising conduit means and heat exchanger means;
   a follow-up esterification reactor having a fixed bed catalyst;
   means for forwarding a current of said alcohol, said acid and ester formed in the pre-reactor from said pre-reactor to said follow-up reactor; and
   means connected to said pre-reactor for recirculating a portion of said alcohol, said acid and said ester to said rotatable tunnel oven.

* * * * *